United States Patent [19]

Arpesella et al.

[11] Patent Number: 5,300,113
[45] Date of Patent: Apr. 5, 1994

[54] CARDIAC VENTRICULAR ASSISTANCE DEVICE PARTICULARLY FOR COMPENSATING FOR WEAKENED HEART MUSCLE FUNCTION AND FOR MAINTAINING THE VITAL BODY FUNCTIONS

[75] Inventors: Giorgio Arpesella, Bologna; Bruno Mambrito, Frascati; Maurizio Zagara, Rome, all of Italy

[73] Assignee: Ministero dell'Universita e della Ricerca Scientifica e Tecnologica, Rome, Italy

[21] Appl. No.: 975,133

[22] Filed: Nov. 12, 1992

Related U.S. Application Data

[63] Continuation of Ser. No. 659,997, Feb. 22, 1991, abandoned.

[51] Int. Cl.$^5$ .................. A61M 1/10; A61N 1/362
[52] U.S. Cl. .................................. 623/3; 600/16; 600/18
[58] Field of Search ............. 623/3; 600/16–18

[56] References Cited

U.S. PATENT DOCUMENTS

| 4,078,267 | 3/1978 | Cieszynski | 623/3 |
|---|---|---|---|
| 4,131,604 | 12/1978 | Szycher | 623/3 |
| 4,453,537 | 6/1984 | Spitzer | 623/3 |
| 4,731,076 | 3/1988 | Noon et al. | 623/3 |
| 4,759,760 | 7/1988 | Snapp, Jr. | 623/3 |
| 4,813,952 | 3/1989 | Khalafalla | 623/3 |
| 4,820,300 | 4/1989 | Pierce et al. | 623/3 |
| 4,822,356 | 4/1989 | Chareire et al. | 623/3 |
| 4,888,011 | 12/1989 | Kung et al. | 623/3 |
| 4,979,936 | 12/1990 | Stephenson et al. | 600/16 |
| 5,089,019 | 2/1992 | Grandjean | 623/3 |
| 5,098,442 | 3/1992 | Grandjean | 623/3 |

FOREIGN PATENT DOCUMENTS

| 0216042 | 4/1987 | European Pat. Off. | 600/16 |
|---|---|---|---|
| 1106511 | 8/1984 | U.S.S.R. | 600/16 |

Primary Examiner—David Isabella
Assistant Examiner—Elizabeth M. Burke
Attorney, Agent, or Firm—Shea & Gould

[57] ABSTRACT

A single cardiac ventricular assistance device intended to integrate the functions of a ventricular assistance device (V.A.D.) proper and of an aortic balloon pump (IABP) includes a single energy source which causes the simultaneous rhythmic contraction of two chambers which are intended to be filled with blood. One of the contractible chambers has two one-way valves for the inlet and outlet of the blood respectively, while the other has a single inlet-outlet connector without valves for connection to the outlet of the first chamber downstream of its outlet-valve portion.

11 Claims, 4 Drawing Sheets

CARDIAC VENTRICULAR ASSISTANCE DEVICE PARTICULARLY FOR COMPENSATING FOR WEAKENED HEART MUSCLE FUNCTION AND FOR MAINTAINING THE VITAL BODY FUNCTIONS

This is a continuation of application Ser. No. 07/659,997, filed Feb. 22, 1991 now abandoned.

BACKGROUND OF THE INVENTION

The present invention relates to devices for use in the treatment of acute or chronic mono- or bi-ventricular myocardial insufficiency.

In general terms, two different kinds of device are known for the treatment of this condition.

The first kind of device is that currently known as an aortic pulsator (an I.A.B.P., that is, an intra-aortic balloon pump).

Its operation is based on the reduction of the so-called post-loading (the overall resistance of the vascular system) in synchronism with the systolic expulsion from the left ventricle in order indirectly to increase the output of the heart.

This device usually takes the form of a hollow catheter with a spindle-shaped balloon about 25-30 cm long at its end which, in its inflated condition, can occupy a volume of about 40 cm$^3$.

The catheter in question is positioned in the thoracic aorta by being passed along the femoral artery. The catheter is connected to a driver unit with a compressor and a system for synchronising it with the patient's electrocardiogram or arterial pressure. The driver unit inflates and deflates the balloon in the thoracic aorta in synchronism with the stages of the heart's activity. In general, at the beginning of the ventricular systole (the emptying of the left ventricle and the corresponding expulsion of a quantity of blood), the intra-aortic balloon is deflated so as to reduce the telediastolic pressure (the "minimum" pressure) which is equivalent to the reduction of the peripheral resistance of the vascular system, that is, the so-called post-loading.

It is thus possible to create conditions favourable to the admission of a greater quantity of blood to the arterial system. The difference between the volume of the systolic output with and without the balloon pump represents the gain in terms of the efficiency of the system (15-20% on average). During the diastole, that is, when the aortic valve is closed, the intra-aortic balloon is inflated and consequently pushes back a quantity of blood approximately equal to its own volume (about 40 cm$^3$) in both a cranial direction (that is, towards the upper part of the body ) and a caudal direction (that is, towards the lower part of the body). This raises the arterial pressure which has the positive result of an increase in the coronary flow-rate.

The other kind of device is essentially that currently known as a ventricular assistance device (V.A.D.). It is based on the bypassing of the right and/or left ventricles by the withdrawal of blood from the atria or directly from the ventricles and its readmission to the pulmonary artery and/or to the aorta.

Devices of this type can be divided further into alternating V.A.D.s (for example, electropneumatic, electromagnetic, electromechanical systems, etc.) which effect intake stages followed by compression stages so as to create a pulsed blood-flow, and continuous V.A.D.s which create a continuous flow by means of a system with a centrifugal pump.

The main advantage of these devices is their ability to keep a patient alive even when the heart has stopped or is fibrillating. For this reason, V.A.D. systems are used most successfully for mechanically supporting circulation whilst a heart transplant is awaited (a transplant bridge).

They have been found to be much less effective, however, when used in parallel with the heart in an attempt to compensate for temporarily weakened heart function.

A plausible explanation for this ineffectiveness is that all V.A.D.s reduce the preloading of the heart muscle but increase the aforementioned post-loading (an increase in the average arterial pressure). With an inadequate ventricle (that is, a ventricle without functional reserve) the increase in the post-loading reduces the volume of blood expelled during the ventricular systole until, in certain extreme cases of weakened contractile activity of the heart, the aortic valve fails to open (the volume of blood expelled is zero). The resulting increased post-systolic volume creates a series of physical-metabolic conditions in the ventricles which create conditions unfavourable to the functional recovery of the heart.

SUMMARY OF THE INVENTION

There is thus a need to provide a device which can simultaneously achieve the following results:

a reduction in preloading by the withdrawal of blood upstream of the ventricles, a blood-flow which can maintain adequate perfusion of a patient's organs even in the absence of heart activity, a reduction in post-loading during systolic expulsion, and an increase in the coronary flow-rate in the diastolic stage.

Briefly, there is a need to provide a device which can combine the advantages of V.A.D. systems and of balloon-pump systems without incurring their respective disadvantages.

The object of the present invention is to provide a device which satisfies this need in an optimum manner.

According to the present invention, this object is achieved by virtue of a device having the characteristics recited in the claims which follow.

The invention will now be described, purely by way of non-limiting example, with reference to the appended drawings, in which:

DESCRIPTION OF THE PREFERRED EMBODIMENTS

Figure 1:
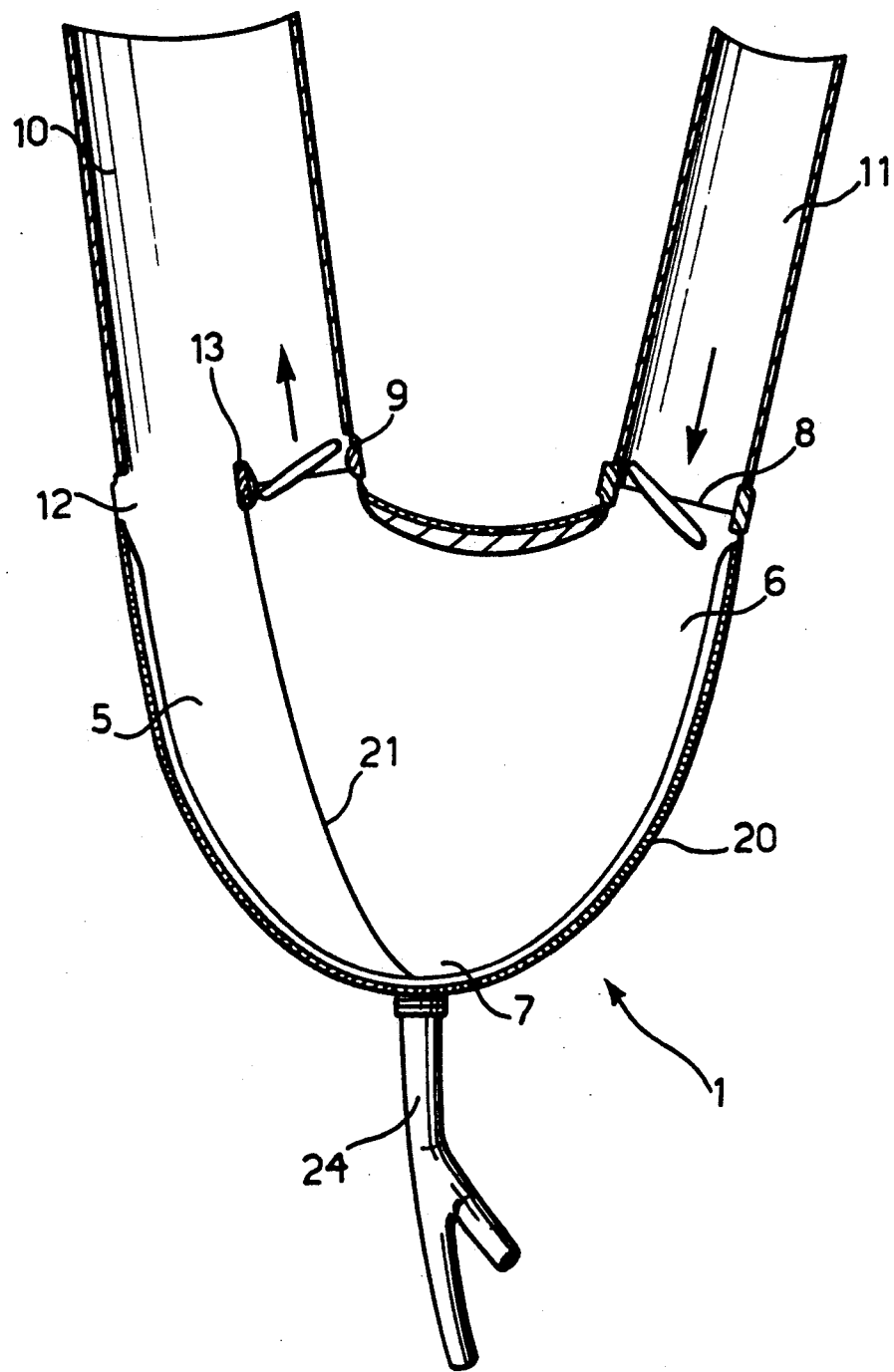
FIGS. 1 and 2 show two possible embodiments of the device according to the invention.
Figure 2:
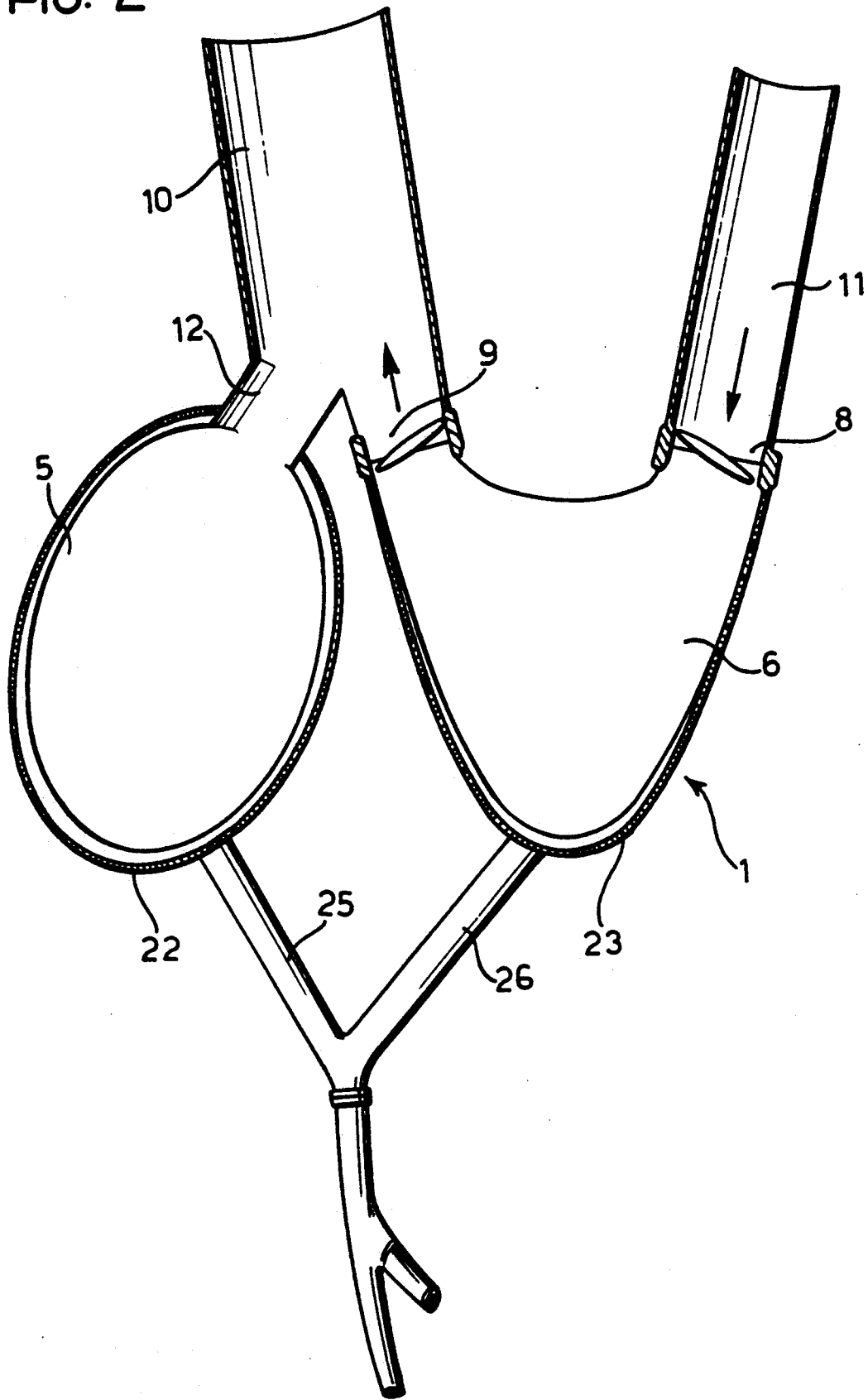

The device according to the invention, generally indicated 1, includes essentially a ventricular bag 6 (the first chamber) with two one-way valves 8 and 9 (constituted, for example, by heart-valve prostheses or valves of a similar structure) whose directions of opening are selected such that the alternate contraction and expansion of the ventricular bag 6 creates a blood-flow in the direction indicated by the arrows in FIGS. 1 and 2. In practice, the valve 8 acts as an inlet valve for admitting blood to the bag 6 and the valve 9 acts as an outlet valve for discharging it therefrom.

Figure 3:
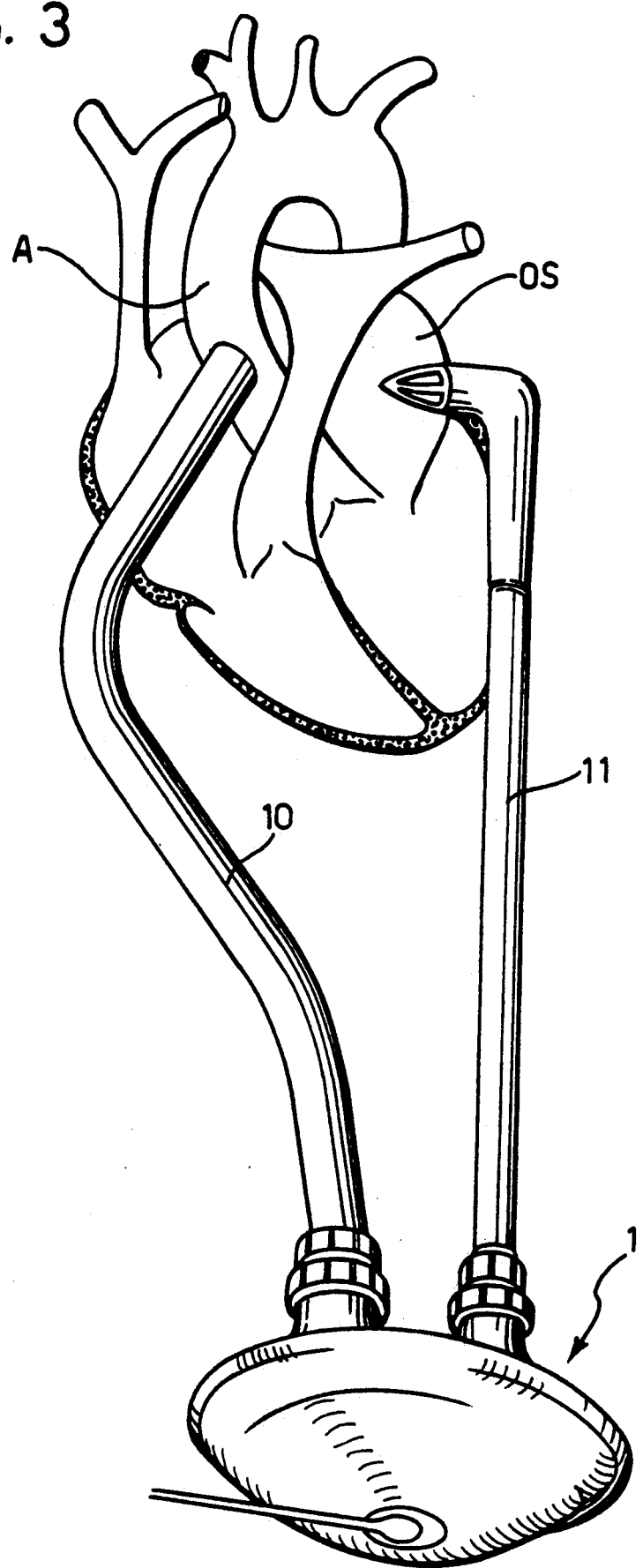
FIGS. 3 and 4 show the general arrangement of the device according to the invention in use and also with reference to its operating sequence.
Figure 4:
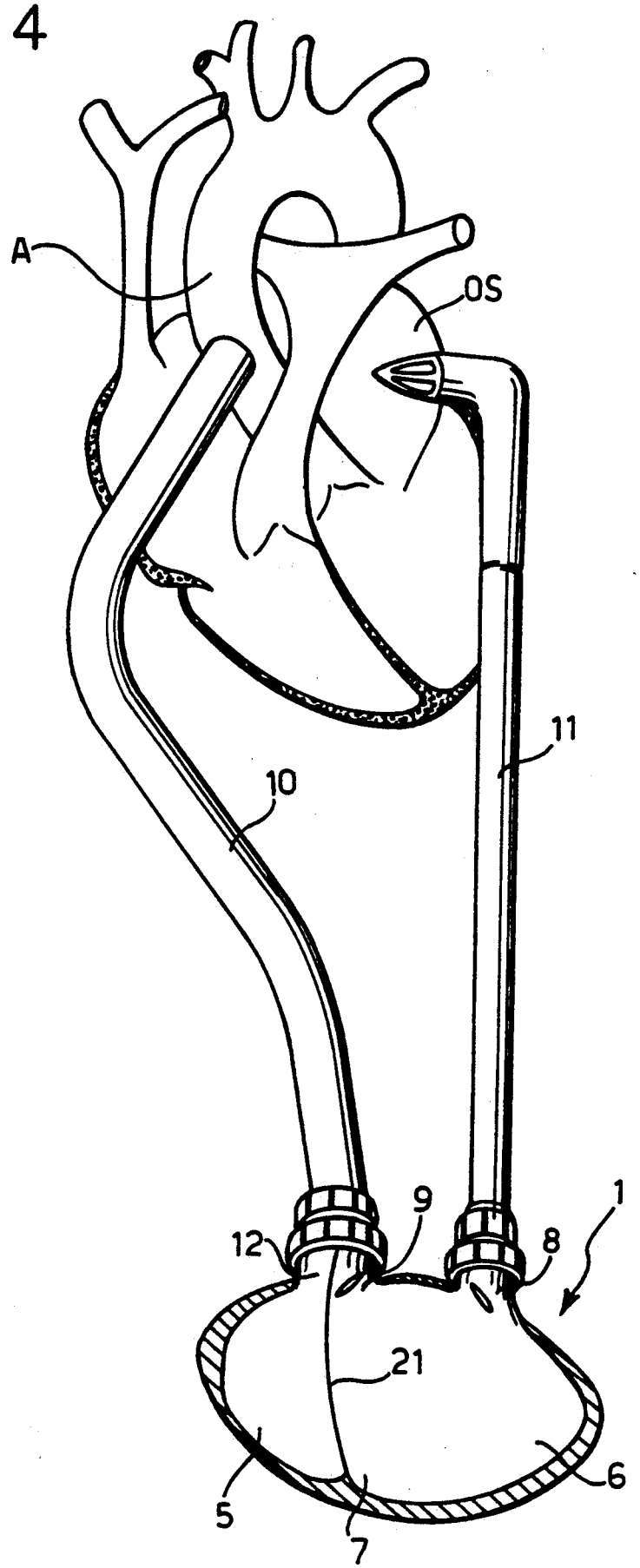

A tube 11 (for example, of the type currently used as a vascular prosthesis (a "vascular graft") is connected to the inlet valve 8 and is intended to be connected to the right or left atrium of the patient's heart according to the arrangement shown in FIGS. 3 and 4.

The outlet valve 9 opens into an outlet tube 10 which has a structure generally similar to that of the tube 11, and is intended to be connected to the patient's pulmonary artery or aorta, again according to the arrangement shown in FIGS. 3 and 4.

A further chamber or bag 5 (the second chamber) is associated with the bag 6, either in one unit (that is, within a single overall envelope 20 according to the arrangement shown in FIG. 1) or in a spatially adjacent arrangement (according to the solution shown in FIG. 2, which has two separate envelopes 22, 23), and has a single, free, communication opening 12, that is, an opening which enables the unimpeded flow of blood out of and into the bag 5, which opens into the tube 10 downstream of the outlet valve 9 with reference to the direction in which the blood is expelled from the bag 6.

If the bags or chambers 5, 6 are housed in a single envelope 20, a soft or partially rigid dividing wall 21 is provided.

Each chamber 5, 6 (which, like the tubes 10, 11 and the valves 8 and 9, are formed according to solutions widely known in the art and do not need to be described fully herein) is defined essentially by a bag, bladder or balloon of flexible material (for example, a polymeric material) housed in an envelope which is essentially rigid or relatively more rigid (the envelope 20 of FIG. 1, the envelopes 22, 23 in the solution of FIG. 2). The outer surface of the bag and the inner surface of its envelope thus define an operating chamber into which an operating or supply source (usually constituted by a pneumatic or hydraulic pump) rhythmically delivers a fluid under pressure through respective supply tubes 24, 25 and 26, causing the flexible walls of the bags to contract and consequently reduce the volumes of the chambers 5 and 6.

The alternating supply and discharge of the pressurised fluid (that is, by a succession of pumping and discharge stages with the consequent alternating contraction and expansion of the bags) results in a pulsed pumping action on the blood circulating in the device 1.

In particular, the chamber 6, which is intended to act as an artificial ventricle, takes in blood—during the expansion stage—from the tube 11 through the inlet valve 8 and then expels that quantity of blood—during the contraction stage—through the valve 9 into the tube 10.

The chamber 5 (which is intended to play a functional role substantially comparable to that of an aortic balloon pump) can vary its volume in order selectively to vary the post-loading of the heart.

The chambers 5, 6 are operated in synchronism by the same fluid supply so that, during their diastolic stage, that is, when the blood is flowing into the chamber 6 through the valve 8, the chamber 5 also expands to reach its maximum volume.

Conversely, when the chamber 6 moves on to the systolic stage and contracts in order to expel the quantity of blood which has previously collected within it, the bag 5 also contracts to reduce its volume.

FIGS. 3 and 4 refer explicitly to a possible arrangement for the connection of the device according to the invention in parallel with the left ventricle.

This means that the inlet tube 11 is connected to the left auricle or atrium whilst the outlet tube 10 is connected to the ascending portion of the aorta A.

The connections are formed according to known criteria, for example, by insertion or anastomosis.

At the beginning of the ventricular systole of the heart, the pneumatic source (the pump) which supplies the tubes 24, 25 and 26 is operated (by a vacuum, spring, etc.) in a condition of active pressure reduction so as to cause the maximum expansion of the chambers 5 and 6 which fill with blood.

In particular, the chamber 6 receives blood from the tube 11 connected to the left atrium, thus reducing the preloading of the ventricle. The chamber 5 which communicates with the aorta A through the tube 10 fills with blood as a result of the pressure gradients prevailing in the two regions (the aorta A and the chamber 5), reducing the post-loading of the left ventricle.

At the end of the ventricular systole of the heart or during the diastole, the operating source supplies the tubes 24, 25 and 26 so that both the chambers 5 and 6 are compressed and the quantity of blood collected therein during the preceding stage is admitted to the aorta A through the tube 10, increasing the arterial pressure with a consequent increase in coronary perfusion.

In the event of heart fibrillation, the chamber 5 does not fulfil an active haemodynamic role and the valved chamber 6 which is arranged to bypass the ventricles can maintain the vital body functions on its own.

It is clear from the foregoing that the device according to the invention simultaneously satisfies, in a wholly satisfactory manner, all the functional requirements which are normally satisfied—separately —by V.A.D.s and aortic balloon pumps, without giving rise to the problems demonstrated by those devices.

Naturally, the principle of the invention remaining the same, the details of construction and forms of embodiment may be varied widely with respect to those described and illustrated, without thereby departing from the scope of the present invention.

What is claimed is:

1. A cardiac ventricular assistance device configured for use in a blood stream, comprising:
   (a) a first selectively contractible artificial chamber for filling with a quantity of blood;
   (b) a first valve means operatively connected with said first chamber for admitting a quantity of blood into said first chamber;
   (c) a second valve means operatively connected with said first chamber for discharging a quantity of blood from said first chamber;
   (d) an outlet tube connected to said second valve means;
   (e) a second selectively contractible artificial valveless chamber having an unimpeded opening connected to said outlet tube downstream of said second valve means whereby said second chamber functions by varying a volume of said second chamber in order to selectively vary post-loading of the heart; and
   (f) an operating means for synchronistically contracting said first and second chambers in a substantially pulsed manner.

2. A device as defined in claim 1 wherein said first and second chambers are contained within a common envelope and separated by a common dividing means.

3. A device as defined in claim 2 wherein said dividing means is soft.

4. A device as defined in claim 2 wherein said dividing means is partially rigid.

5. A device as defined in claim 1 wherein said first and second chambers are contained within separate envelopes.

6. A device as defined in claim 5 wherein at least one of said chamber envelopes is comprised of a flexible material.

7. A device as defined in claim 5 wherein at least one of said chamber envelopes is comprised of a rigid outer envelope and an inner membrane of flexible material.

8. A device as defined in claim 6, wherein said envelope of flexible material is housed within a rigid envelope.

9. A device as defined in claim 8, wherein said envelope of flexible material comprises an outer surface and said rigid envelope comprises an inner surface wherein said outer surface and said inner surface define an operating chamber for receiving a pressurized fluid from said operating means.

10. A device as defined in claim 1 wherein said first and second valve means comprise pivoting obturators.

11. A device as defined in claim 2 wherein said operating means further comprises a single tube for supplying a pressurized fluid to said common envelope.

* * * * *

UNITED STATES PATENT AND TRADEMARK OFFICE
CERTIFICATE OF CORRECTION

PATENT NO. : 5,300,113
DATED : April 5, 1994
INVENTOR(S) : Giorgio Arpesella, Bruno Mambrito and Maurizio Zagara It is certified that error appears in the above-indentified patent and that said Letters Patent is hereby corrected as shown below:

On the title page,
[30]  Foreign Application Priority Data

March 20, 1990  [IT]  Italy ..................67204-A/90

Signed and Sealed this

Tenth Day of June, 1997

Attest:

BRUCE LEHMAN

Attesting Officer

Commissioner of Patents and Trademarks